(12) United States Patent
Omura

(10) Patent No.: US 6,303,144 B1
(45) Date of Patent: Oct. 16, 2001

(54) PREPARATIONS WITH CONTROLLED RELEASE

(75) Inventor: Tomoyuki Omura, Chikujo-gun (JP)

(73) Assignee: Welfide Corporation, Osaka (JP)

( * ) Notice: Subject to any disclaimer, the term of this patent is extended or adjusted under 35 U.S.C. 154(b) by 0 days.

(21) Appl. No.: 09/601,972

(22) PCT Filed: Feb. 10, 1999

(86) PCT No.: PCT/JP99/00570

§ 371 Date: Aug. 10, 2000

§ 102(e) Date: Aug. 10, 2000

(87) PCT Pub. No.: WO99/40942

PCT Pub. Date: Aug. 19, 1999

(30) Foreign Application Priority Data

Feb. 10, 1998 (JP) .................................. 10-028365

(51) Int. Cl.$^7$ ................ A61K 9/52; A61K 9/48; A61K 9/20; A61K 9/22

(52) U.S. Cl. ................ 424/457; 424/451; 424/453; 424/454; 424/464; 424/468; 514/964

(58) Field of Search .................... 424/451, 468, 424/453, 464, 454, 457; 514/964

(56) References Cited

U.S. PATENT DOCUMENTS

| | | | |
|---|---|---|---|
| 4,432,966 | 2/1984 | Zeitoun et al. | 424/21 |
| 5,028,664 | 7/1991 | Ohmura et al. | 525/217 |
| 5,137,733 | 8/1992 | Noda et al. | 424/497 |
| 5,258,186 | 11/1993 | Ohmura et al. | 424/497 |

FOREIGN PATENT DOCUMENTS

| | | |
|---|---|---|
| 0040590 | 11/1981 | (EP) . |
| 0754452 | 1/1997 | (EP) . |
| 2283912A * | 5/1995 | (GB) . |
| 2-58246 | 12/1990 | (JP) . |
| 3-7238 | 1/1991 | (JP) . |
| 4-501411 | 3/1992 | (JP) . |
| 4-235123 | 8/1992 | (JP) . |
| 4-264022 | 9/1992 | (JP) . |
| 4-505004 | 9/1992 | (JP) . |
| 8-1437476 * | 6/1996 | (JP) . |
| 8-143476 | 6/1996 | (JP) . |
| 9-87169 | 3/1997 | (JP) . |
| 90/04396 | 5/1990 | (WO) . |
| 90/09168 | 8/1990 | (WO) . |
| WO 90/09168 * | 8/1990 | (WO) . |
| 94/09745 | 5/1994 | (WO) . |
| 94/09746 | 5/1994 | (WO) . |

\* cited by examiner

*Primary Examiner*—James M. Spear
*Assistant Examiner*—Rachel M. Bennett
(74) *Attorney, Agent, or Firm*—Wenderoth, Lind & Ponack, L.L.P.

(57) ABSTRACT

A controlled release preparation containing at least one kind of a pharmaceutically active ingredient, a male piece and a female piece, the pieces fitting together to enclose the active substance therein, wherein the male piece is made from a material that gels in the intestinal juice, is disclosed. In a preferable mode, the male piece contains an ethyl acrylate-methyl methacrylate-trimethylammonioethyl methacrylate chloride copolymer and a methacrylic acid-ethyl acrylate copolymer. In a preferable mode, the female piece is made from a water insoluble polymer. In a preferable mode, the dosage form is a tablet or a capsule. The controlled release preparation of the present invention does not at all release a drug in the region having a low pH, such as in the stomach, but only in the region having a pH relatively near the neutral range, such as in the small bowel and the large bowel, the plug gradually gels from the upper surface and, after a given time when a part of the male piece (plug) having the least thickness gels and has become permeable, concurrently releases the drug in a short time in a pulse manner. Consequently, the drug can act effectively at a local site in the lower part of the small bowel, the large bowel and the like, and a drug can be delivered to the lower part of the small bowel or the large bowel without undergoing decomposition of peptides and proteins.

8 Claims, 2 Drawing Sheets

PREPARATIONS WITH CONTROLLED RELEASE

This application is a 371 application of PCT/JP99/00570 filed Feb. 10, 1999.

1. Technical Field

The present invention relates to a novel preparation used for controlling the release of an active substance, particularly a pharmaceutically active ingredient. More particularly, the present invention relates to a preparation suitable for releasing a drug in a comparatively short time following a given period of lag time (time during which a drug is not released) after administration, namely, a pulse release preparation.

2. Background Art

In the treatment using drugs, a selective delivery of a drug to the lower part of the small bowel and the large bowel is desired in the fields of (1) a local treatment of inflammatory bowel diseases such as ulcerative colitis, (2) a treatment by oral administration of a peptide drug which is susceptible to chemical decomposition and enzymatic degradation in the small bowel, and the like. For a selective drug delivery to the lower part of the small bowel and the large bowel, therefore, the preparation design in recent years involves consideration of the physical and physiological environment in the gastrointestinal tract of humans and the time necessary for the transfer of the preparation within the gastrointestinal tract.

For instance, conventional enteric preparations and sustained release preparations are not designed from these viewpoints. As a result, although the former preparation effectively inhibits the dissolution of a drug in the stomach, it fails to deliver the drug to the large bowel, because the drug is rapidly dissolved in the upper part of the small bowel and mostly absorbed or decomposed there. The latter preparation is associated with a problem in that a considerable part of the drug is dissolved during the passage of the preparation through the stomach and the small bowel, because the drug is dissolved in a sustained manner.

In addition, preparations having a release control film made from a water insoluble polymer and an enteric polymer in combination are known (JP-A-3-7238, EP-B-40590). In these preparations, a drug is gradually dissolved after oral administration or after transfer into the small bowel, which means that the time of start of dissolution and pH at which the dissolution is started are not controlled, thus failing to direct the drug concentratively to the lower part of the gastrointestinal tract.

In view of the above-mentioned defects of the conventional enteric preparations and sustained release preparations and with the aim of providing a higher level and higher performance drug delivery system targeting a specific region of an appropriate part in the gastrointestinal tract (particularly, lower part of the gastrointestinal tract, such as the small bowel, the large bowel and the like), a new controlled release preparation that enables accurate drug release at this region is being developed.

As an oral administration system to release a drug site-specifically at various lower parts of the gastrointestinal tract based on a preparation formulation method, for example, there have been known a method for controlling the release start time by utilizing the time necessary for transfer of the preparation in the gastrointestinal tract, a method for determining the release site by utilizing enterobacteria, and other methods.

JP-B-2-58246 discloses a compressed tablet that is specifically disintegrated in the colon to release an active ingredient, irrespective of the length of drug residence time in the stomach. Because this compressed tablet utilizes bacteria present in the colon, however, the time of disintegration varies depending on the inter-individual difference in the bacteria present in the colon, and the decomposition takes defectively long when the enterobacteria have a lower decomposition activity.

JP-A-4-235123 discloses a controlled release preparation having a film coating made from an ethyl acrylate-methyl methacrylate-trimethylammonioethyl methacrylate chloride copolymer (Eudragit RS; trademark, Röhm Pharma) and a water-repellent salt (calcium stearate). This is a so-called sigmoid type controlled release preparation that releases a pharmaceutical compound after a given time. This preparation controls the time before the start of dissolution by controlling the water-permeation rate of the film coating, and requires an accurate control of the amount of the film coating, so as to appropriately control the time before the start of dissolution. The preparation also has a defect in that a thicker film makes quick dissolution of the drug after the start of the dissolution difficult to achieve. Moreover, the system of this preparation involves a drug release after a given time from the oral administration of the preparation, which makes it difficult to specify the site where the release occurs.

JP-A-4-264022 discloses an oral preparation for release in the lower part of the gastrointestinal tract, which is obtained by filling a hard capsule made from a base mainly composed of chitosan with a solid preparation containing a solid organic acid and the principal agent ingredient, and forming an enteric film e coating on the surface of the capsule. This preparation controls the time before the start of dissolution by changing the thickness of the hard capsule, and requires an accurate control of the thickness of the capsule wall for controlling the dissolution start time.

Japanese Patent Application under PCT laid-open under kohyo No. 4-505004 discloses a controlled release preparation based on the system wherein a water insoluble capsule is capped with a water swellable plug, and the plug begins to swell upon water absorption, and, after a given time, comes out to release the drug in the capsule. This preparation employs a system of releasing a drug after a given time from oral administration. This makes specification of the release site in the gastrointestinal tract very difficult, because the residence time of the preparation in the stomach varies due to the inter-individual difference.

These conventional enteric preparations for topical treatment are defective because they have complicated structures and the time before the start of dissolution varies depending on pH and inter-individual difference in the residence time in the stomach and the like, which in turn makes the control of the lag time difficult and makes these preparations insufficient to achieve an effective blood concentration by quick dissolution of the entire amount of the drug after the start of dissolution.

As a system that utilizes the transfer time of a preparation in the gastrointestinal tract, several systems based on the transfer time in the small bowel, that disregards the variation in the residence time of the preparation in the stomach, have been developed noting the fact that the passage of the preparation through the small bowel takes almost the same length of time for any individual. These systems are free of drug release during the intragastric residence time and enable a specified release of the drug after a certain time after transfer into the small bowel following discharge from the stomach, namely, at a site a certain distance away from the stomach, such as in the large bowel which is in the lower part of the gastrointestinal tract.

To be specific, for example, JP-A-4-501411 discloses a preparation that releases a drug after a given lag time, which is achieved by applying a three-layer coating comprising an inner layer coated with an anionic copolymer that dissolves at a pH of not less than 7.0, an intermediate layer comprising a gelling polymer that swells and gels in a pH non-dependent manner to form a gel layer, and an outer layer comprising an appropriate amount of a stomach resistant polymer that quickly dissolves in the bowels. However, this preparation is defective in that the dissolution rate of the gelling polymer often changes due to the kinetics within the gastrointestinal tract, resulting in inconsistent lag time, and the system is extremely complicated both in the structure and production method, as mentioned in the above.

Besides the above-mentioned, there has been disclosed a large bowel delivery system comprising the aforementioned preparation of Japanese Patent Application under PCT laid-open under kohyo No. 4-505004 applied with an enteric film coating; JP-A-8-143476 discloses a preparation applied with an acrylate polymer mixture film coating; and JP-A-9-87169 discloses a system wherein a capsule containing an acidic substance is coated with a low pH soluble film and an enteric film.

As the situation stands, a system having both the function of an enteric film coating and the function of controlling the drug release time is structurally very complicated and requires time and labor for the production.

The present invention aims at providing a preparation capable of releasing a drug rapidly at a predetermined time and pH.

DISCLOSURE OF THE INVENTION

The present inventor has conducted intensive studies to develop a preparation for oral administration, which does not release a drug until it reaches a specific site in the lower part of the gastrointestinal tract, such as the small bowel, the large bowel and the like, and, upon delivery to the intended site, quickly releases the entire amount of the drug in a pulse manner, and found that a preparation comprising at least two mutually fitting pieces, wherein a female piece enclosing an active substance is plugged with a male piece (plug) made from a material that gels in the intestinal juice, does not release the drug at all in a low pH range, such as in the stomach, but only in the region having a pH relatively near the neutral range, such as in the small bowel and the large bowel, the male piece gradually gels from the side in contact with the intestinal juice, and, after a given time when a part of the male piece having the smallest thickness gels and has become permeable, releases the drug in a pulse manner in a short time, which resulted in the completion of the present invention.

The controlled release preparation of the present invention comprises at least one kind of a pharmaceutically active ingredient, a male piece and a female piece, the male and female pieces being fitted together to enclose the active substance and the male piece being made from a material that gels in the intestinal juice.

In a preferable mode, the male piece contains, as the material that gels in the intestinal juice, an ethyl acrylate-methyl methacrylate-trimethylammonioethyl methacrylate chloride copolymer and a methacrylic acid-ethyl acrylate copolymer.

The above-mentioned ethyl acrylate-methyl methacrylate-trimethylammonioethyl methacrylate chloride copolymer more preferably has a copolymerization ratio (ethyl acrylate:methyl methacrylate:trimethylammonioethyl methacrylate chloride (molar ratio)) of about 1:2:0.1–0.2, and the methacrylic acid-ethyl acrylate copolymer more preferably has a copolymerization ratio (methacrylic acid-:ethyl acrylate (molar ratio)) of about 1:1.

The methacrylic acid-ethyl acrylate copolymer is more preferably contained in a proportion of 0.3–20 parts by weight per part by weight of the above-mentioned ethyl acrylate-methyl methacrylate-trimethylammonioethyl methacrylate chloride copolymer.

In a preferable mode of the controlled release preparation of the present invention, the female piece is made from a water insoluble polymer.

Moreover, in a preferable mode of the controlled release preparation of the present invention, the dosage form is a tablet or capsule.

DETAILED DESCRIPTION OF THE INVENTION

Figure 1:
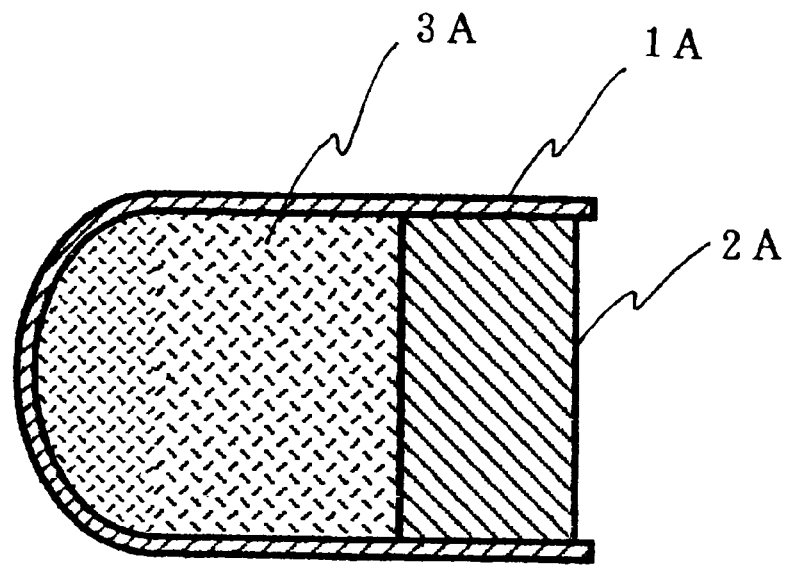
FIG. 1 is a schematic showing of the preparation (capsule) of the present invention.

The present invention provides a controlled release preparation containing an active ingredient, which is made of at least two mutually fitting pieces containing the active substance therein, wherein the male piece is formed from a material that gels in the intestinal juice. The preparation shows no changes in the shape in the gastric juice having a low pH and gradually gels and becomes permeable only when it gets wet with the intestinal juice having a high pH (pH of not less than 5.5).

The preparation of the present invention has, for example, 1 or 2 openings in the female piece and the aforementioned openings are preferably closed with a plug made from a material that gels in the intestinal juice. In this case, the aforementioned plug gels and becomes permeable from the surface upon immersion in the intestinal juice, and when the thinnest part has become a gel, the active substance is concurrently released into the surrounding environment in a pulse manner.

The male piece to be used for the preparation of the present invention is made from a material that gels in the intestinal juice. The material that gels in the intestinal juice is preferably a mixture of an ethyl acrylate-methyl methacrylate-trimethylammonioethyl methacrylate chloride copolymer and a methacrylic acid-ethyl acrylate copolymer. Particularly, a mixture of an ethyl acrylate-methyl methacrylate-trimethylammonioethyl methacrylate chloride copolymer having a copolymerization ratio (ethyl acrylate-:methyl methacrylate:trimethylammonioethyl methacrylate chloride (molar ratio)) of about 1:2:0.1–0.2 and a methacrylic acid-ethyl acrylate copolymer having a copolymerization ratio (methacrylic acid:ethyl acrylate (molar ratio)) of about 1:1 is more preferably used.

Specific examples of the ethyl acrylate-methyl methacrylate-trimethylammonioethyl methacrylate chloride copolymer having a copolymerization ratio (ethyl acrylate-:methyl methacrylate:trimethylammonioethyl methacrylate chloride (molar ratio)) of about 1:2:0.1–0.2 include Eudragit RS (Eudragit RS:trademark, manufactured by Röhm Pharma) series, and examples of the copolymer having a copolymerization ratio of about 1:2:0.1 include Eudragit RS100 (granules), RSPO (fine powder), RS30D (solid content 30%, aqueous dispersion) and the like, with particular preference given to Eudragit RS100 and RSPO. Examples of the copolymer having a copolymerization ratio of about 1:2:0.2 include Eudragit RL100 (granules), RLPO (fine powder), RL30D (solid content 30%, aqueous dispersion) and the like, with particular preference given to Eudragit RL100 and RLPO.

Specific examples of the methacrylic acid-ethyl acrylate copolymer having a copolymerization ratio (methacrylic acid:ethyl acrylate (molar ratio)) of about 1:1 include Eudragit LD (Eudragit LD:trademark, manufactured by Röhm Pharma) series, with preference given to Eudragit L100-55 (fine powder) and L30D-55 (solid content 30%, aqueous dispersion), and particular preference given to Eudragit L100-55.

In the present invention, the mixing ratio of the both of the above-mentioned copolymers in the male piece is not particularly limited as long as the both copolymers are contained. In general, the suitable proportion is 0.3–20 parts by weight, preferably 0.4–15 parts by weight, particularly preferably 0.5–10 parts by weight, of the methacrylic acid-ethyl acrylate copolymer per part by weight of the ethyl acrylate-methyl methacrylate-trimethylammonioethyl methacrylate chloride copolymer. The male piece may contain various agents typically used in this field such as excipient, binder, lubricant, coagulation preventive, solubilizer of the pharmaceutical compound and the like to be mentioned below.

When the preparation is used as a preparation for oral administration, the female piece may be formed from a material biologically and medically compatible, non-allergic, and nonirritative to the body fluids and biological tissues. The female piece can be produced from a water impermeable or water permeable material as a starting material, with preference given to a water impermeable material. When a water permeable material is used, a material that prevents permeation of a liquid solution or intestinal juice, with which the male piece is gelled, is preferable. The female piece is preferably formed from a water non-swellable material.

As the water impermeable material and water permeable material to be used for forming the female piece, a water insoluble polymer is used, which is selected from polyethylene, polypropylene, polymethyl methacrylate, polyvinyl chloride, polyvinyl acetate, polystyrene, polyurethane, polyester, cellulose acetate, nitrocellulose, ethyl cellulose, and similar materials used for the ethyl acrylate-methyl methacrylate-trimethylammonioethyl methacrylate chloride copolymer and the plug. One or more kinds of the water insoluble polymers can be used. The female piece may have a uniform structure or laminate structure comprising a plurality of different material layers.

In addition, the female piece can be made from a biodegradable material (e.g., azo polymer, polysaccharide and the like that are decomposed by enterobacteria) or a water soluble material (e.g., gelatin, starch, hydroxypropylcellulose, methylcellulose, hydroxypropylmethylcellulose, polyvinyl alcohol and the like), as long as the structural strength can be maintained at least for the lag time. When the wall of the female piece does not have a uniform structure, the wall part forming the opening is preferably made from a water non-swellable material.

It is also possible to form the main part of the female piece from a biodegradable or water soluble material, and the outside and/or inside thereof may be coated with a water insoluble film. In this case, almost all surfaces of the outside is coated and at least the part of the inside that comes into contact-with the male piece is preferably coated, though the entirety of the inside may be coated. It is more preferable to coat not only the outside and the inside, but also an end of the wall of the opening in the body of the female piece, with a water insoluble film. In short, it should be prevented that the body of the female piece made from a biodegradable material or water soluble material be decomposed or swell (dissolve) to cause dissociation of the male piece from the female piece before release of the drug by the gelation of the male piece. The coating layer can be formed by immersing the body of the piece made from a biodegradable or water soluble material in a solution of the water insoluble polymer exemplified above to form a water insoluble layer, or by spraying a solution of the water insoluble polymer exemplified above onto the body of the piece made from a biodegradable material or water soluble material. Examples of preferable female piece include one obtained by coating a typical hard gelatin or starch capsule, as the body of a piece, with an ethylcellulose solution, polyvinyl acetate solution or a polymer similar to the material used for the above-mentioned male piece, one obtained by coating a capsule made from a water soluble material, as the body of a piece, with the aforementioned biodegradable material, and the like.

The female piece is formed to have a shape convenient as a preparation, such as ellipsoidal shape, spheroidal shape, cylindrical shape and the like. A cylindrical capsule is generally preferred but a different shape may be employed. The preparation of the present invention preferably comprises a cylindrical female piece having one open end or both open ends, and a plug (a male piece) made from a material that gels in the intestinal juice set in the one open end or both open ends. Such preparation can be easily formed from an extrusion-formed plastic tube cut in a certain length, with one end optionally sealed and the open end or both ends closed by insertion of plug(s). In addition, the female piece can be prepared by forming a cylinder around a rod mold, applying a polymer solution and the like onto a forming mold, compression forming or injection forming of a suitable thermoplastic polymer, compression forming of a powder, direct reaction forming and the like.

The male piece (plug) can be inserted so as to make the summit thereof on the same plane with the end of the opening of the female piece; inserted so as to make the summit thereof protruding from the end of the opening to the extent that the protrusion prevents dissociation of the plug; or inserted to a depth that makes the cylindrical wall of the female piece extend beyond the summit of the plug. The plug is conveniently of a cylindrical shape, which can be obtained easily by cutting a rod material obtained by forming the aforementioned material, that gels in the intestinal juice, in the shape of a rod. It can be also formed easily using a tablet compressor and the like, which is typically used for the preparation of pharmaceutical products. The plug may have a concave shape with a cavity of a certain depth made therein. It may have a shape like a tablet having a cleavage line of a V shape groove. It may have a different shape such as a conical section. The ratio of length and diameter (length:diameter) of the cylindrical plug is preferably, but not limited to, in the range of from 0.1:10 to 20:1, more preferably from 0.2:10 to 3:1.

Figure 2:
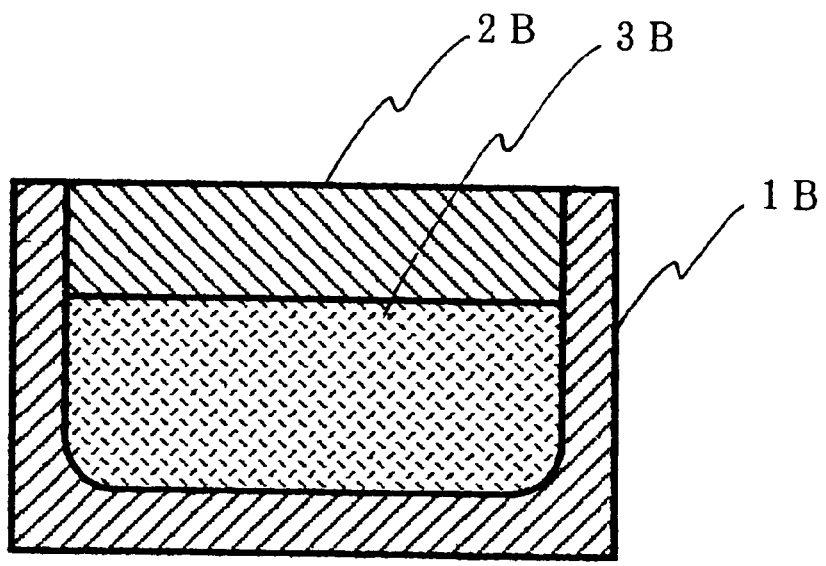
FIG. 2 is a schematic showing of the preparation (tablet) of the present invention.

When a cylindrical preparation is produced, the preparation is beneficially of a size that allows swallowing. Such preparation advantageously serves for a preparation for oral administration particularly to human, and also to animals. The length of the hollow cylinder is typically 5–50 mm, preferably 10–30 mm, and the outer diameter is in the range of from 1 mm to 20 mm. The preparation generally has an outer diameter equivalent to that of known preparations for oral administration. For example, the capsule has a size within the range of from triple zeros to zero and from 1 to 8. The length of the male piece (plug) then is preferably, but not limited to, from 1 mm to 10 mm. FIG. 1 shows one embodiment of the preparation of the present invention when it is made into a capsule, wherein a water insoluble capsule (a female piece) 1A has one closed end and the other open end, a plug (a male piece) 2A, that gels in the intestinal juice, is fitted into the opening, and a drug 3A is sealed in the capsule. FIG. 2 shows one embodiment of the preparation of the present invention when it is made into a tablet, wherein a drug layer 3B and a plug (a male piece) layer 2B, that gels in the intestinal juice, are sequentially fitted into the water insoluble tablet outer layer (a female piece) 1B. The tablet shown in FIG. 2 can be produced by, for example, compression molding the male piece layer and the drug layer into a two-layer tablet and forming an outer layer by a conventional compression-coating tablet machine.

The material constituting the male piece, that gels in the intestinal juice, enables adjustment of the time of delay in the release (lag time) of the contents after immersion into the intestinal juice. The gelling rate and permeability of the material are the important parameters in determining the lag time of the preparation. For example, the mixing ratio of the methacrylic acid-ethyl acrylate copolymer to the ethyl acrylate - methyl methacrylate-trimethylammonioethyl methacrylate chloride copolymer exemplified as a preferable material, that gels in the intestinal juice, as mentioned above, is increased to raise the gelling rate and the permeability, thereby shortening the lag time. In other words, the lag time of the preparation is in reciprocal proportion to the gelling rate and the permeability of the male piece. By changing the thickness of the male piece, the lag time can be also changed. The lag time is in proportion to the thickness of the thinnest part of the male piece. To be more specific, it is in proportion to the thickness of the thinnest part of a plug which is the male piece.

As mentioned above, in the preparation of the present invention, the lag time from the immersion in the intestinal juice to the drug release due to gelation of the plug, and acquired permeability can be varied by adjusting at least one of the above-mentioned parameters; namely, the gelling rate and the permeability of the material constituting the male piece, that gels in the intestinal juice, and the thickness of the male piece. The lag time can vary over a broad range of time of from 30 min to 24 hr depending on the utility. In general terms, when the lower part of the gastrointestinal tract or the large bowel is the delivery site, the target lag time is desirably set to 3–4 hours which is the time of transfer of the preparation in the small bowel.

The preparation is preferably constituted to make the conjunction between a male piece and a female piece completely watertight throughout the release delay period. The wall of the female piece is constituted to ensure structural association with the male piece until at least the thinnest part of the male piece gels and becomes permeable. This means that the male piece and the female plug should stay undetached and adhered until the drug release begins. The present invention differs in this aspect from Pulsincap (controlled release preparation described in Japanese Patent Application under PCT laid-open under kohyo No. 4-505004) that allows separation of a plug (male piece) from a female piece on the way.

The contents of the preparation are, for example, an active substance in the form of solid particles, or an active substance in a different and convenient administration form. For example, the active substance, in combination with typical additives for pharmaceuticals, can be enclosed in the preparation as a powder, fluid solution or suspension. Note that the fluid medium should not interact with the material used for the formation of a female piece or a male piece. It can take the form of a compression formed tablet containing an excipient and the like, which may enclose a single tablet or a plurality of such tablets. Examples of the additives for pharmaceuticals include excipient, binder, lubricant, coagulation preventive, solubilizer of a pharmaceutical compound and the like, that are typically used in this field. Examples of the excipient include sugars such as sucrose, lactose, mannitol, glucose and the like, starches, crystalline cellulose, calcium phosphate, calcium sulfate and the like, and examples of the binder include polyvinyl alcohol, polyacrylic acid, polymethacrylic acid, polyvinylpyrrolidone, glucose, sucrose, lactose, maltose, dextrin, sorbitol, mannitol, hydroxyethylcellulose, hydroxypropylmethylcellulose, hydroxypropylcellulose, macrogols, gum arabic, gelatin, agar, starches and the like. Examples of the lubricant and coagulation preventive include talc, magnesium stearate, calcium stearate, colloidal silica, stearic acid, waxes, castor oil, polyethylene glycols, sodium benzoate and the like. Examples of the solubilizer of a pharmaceutical compound include organic acids, such as fumaric acid, succinic acid, malic acid, adipic acid and the like, various surfactants, such as sodium laurylsulfate and the like, aromatic, coloring matter and the like.

As mentioned above, the preparation comprising at least two mutually fitting pieces does not release a drug until it reaches a specific site in the lower part of the gastrointestinal tract, such as the small bowel, the large bowel and the like, and once it reaches the site, can release the entire amount of the drug quickly in a pulse manner, by only plugging the water insoluble female piece, which contains the active substance, with the male piece (plug) made from a polymer that gels in the intestinal juice. In other words, the preparation of the present invention does not at all release a drug in the region having a low pH, such as in the stomach, but only in the region having a pH relatively near the neutral range, such as in the small bowel and the large bowel, the plug gradually gels from the upper surface and, after a given time when a part of the male piece (plug) having the least thickness gels and has become permeable, concurrently releases the drug in a short time in a pulse manner.

The kind of the drug to be used as the active substance of the pulse release preparation of the present invention is subject to no particular limitation as long as it can be administered orally. Examples of such pharmaceutical compound include chemotherapeutics, antibiotics, respiratory stimulants, antitussive expectorantia, antineoplastic agent, agent for autonomic nerve, agent for neurosis, topical anesthetic, muscle relaxant, agent for digestive organ, antihistamines, therapeutics for toxicosis, sedative hypnotic, antiepileptic agent, antipyretic analgesic antiphlogistics, cardiotonic, antiarrhythmic agent, diuretic, vasodilator, antilipemic agent, analeptic alterant, anticoagulant, agent for liver, hypoglycemic agent, hypotensive agent, therapeutics for colitis, peptide, protein and the like. Among others, the present invention is suitable for a therapeutic for colitis, a therapeutic agent for Crohn's disease, which require efficient action on the lesion in the lower part of the small bowel and the large bowel, and peptide and pharmaceutical protein products susceptible to decomposition in the stomach.

EXAMPLES AND EXPERIMENTAL EXAMPLES

The present invention is explained in detail by referring to Example and Experimental Example that do not limit the present invention in any way.

Example 1

A series of preparations were produced, which comprised a cylindrical capsule (a female piece) whose open end was closed by a plug (a male piece) having a suitable diameter.

Preparation of plug

Talc (50 g) was placed in a fluidized bed granulator (MP-01 type) and fluidized. Thereonto was spray-granulated a solution of Eudragit RSPO (15 g, manufactured by Röhm Pharma), Eudragit L100-55 (35 g, manufactured by Röhm Pharma), triethyl citrate (5 g), talc (50 g), ethanol (900 g) and water (100 g) to give granules. To the granules (155 g) was added and mixed magnesium stearate (0.7 g) to give a powder for compression. Using a tableting machine (CLEANPRESS Correct 12HUK;Kikusui Seisakusho Ltd.) and a plane pestle, 100 mg tablets having a diameter of 6 mm were tableted. A 4 mm diameter cavity having a given depth was made in the tablets to give concave tablets (plugs) having a minimum bottom thickness of about 400 $\mu$m, 500 $\mu$m or 600 $\mu$m.

Production of preparation

Female pieces were obtained by coating the inside and outside of gelatin capsules (No. 2, manufactured by Warner-Lambert) with ethylcellulose. Acetoaminophene (50 mg) and croscarmellose sodium (50 mg) as a disintegrant were enclosed inside the capsules. The opening of the capsules was closed with the plug prepared in the above to give the preparations of the present invention. That is, three kinds of preparations including a preparation containing a plug having a minimum bottom thickness of about 400 $\mu$m, a preparation containing a plug having a minimum bottom thickness of about 500 $\mu$m and a preparation containing a plug having a minimum bottom thickness of about 600 $\mu$m were obtained.

Experimental Example 1

Figure 3:
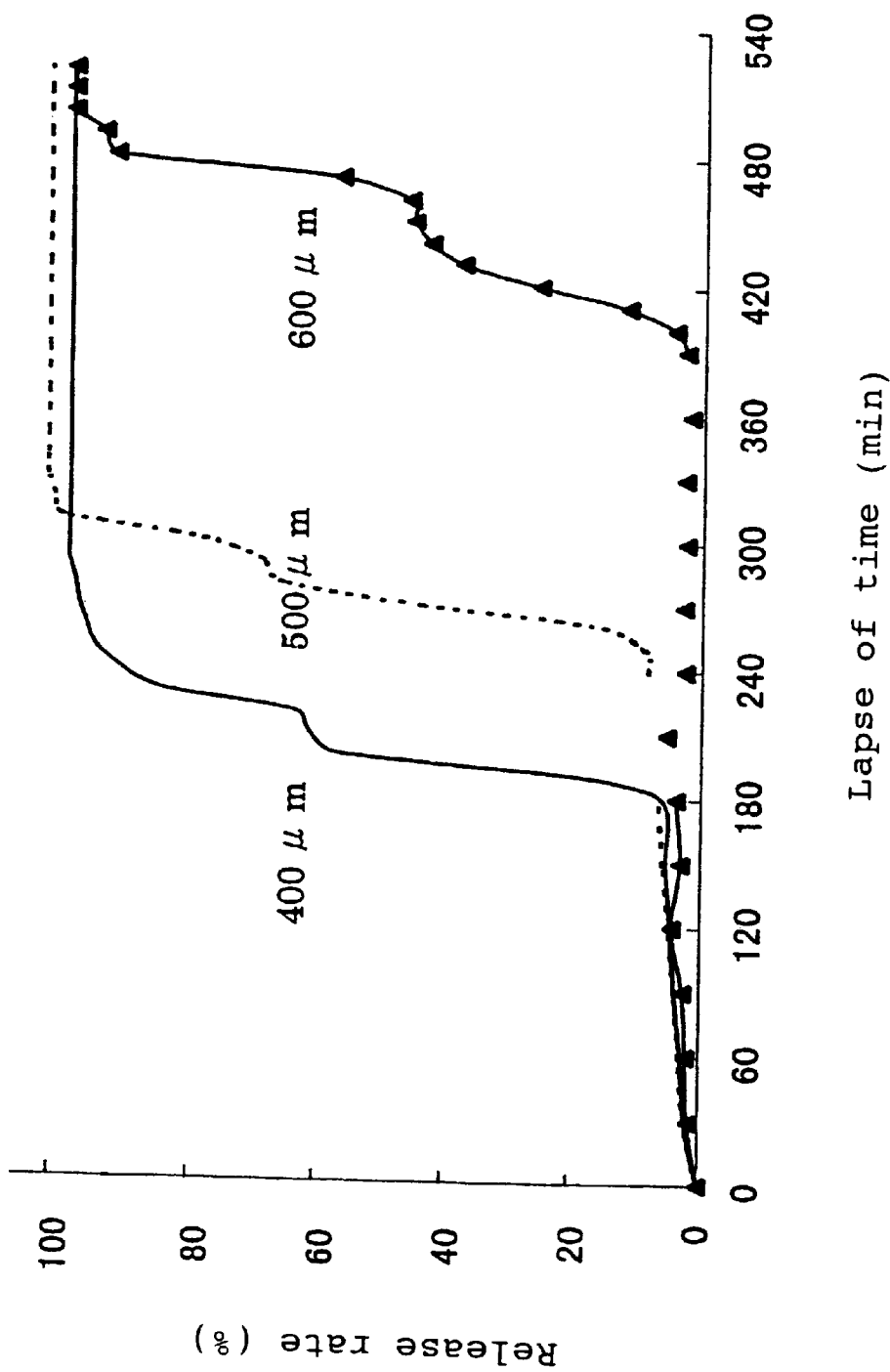
FIG. 3 shows the results of a drug dissolution test in Japanese Pharmacopoeia 2nd Fluid in Experimental Example 1.

The three kinds of preparations obtained in the above-mentioned Example 1 were subjected to the dissolution test using Japanese Pharmacopoeia 1st Fluid (pH 1.2) and 2nd Fluid (pH 6.8) according to the paddle method (37° C., 50 rpm) described in the Japanese Pharmacopoeia. According to the test results, the preparations obtained in Example 1 showed no dissolution of the drug in 1st Fluid. As shown in FIG. 3, the lag time until the start of the dissolution varied in 2nd Fluid according to the thickness of the bottom of the plug. Despite the variation in the lag time, the entirety of the drug was quickly released to 100%, demonstrating the pulse type dissolution pattern. The figures ($\mu$m) attached to the characteristic line in FIG. 3 show the minimum bottom thickness of the plug used for each preparation.

Industrial Applicability

The controlled release preparation of the present invention is characterized in that it shows, after oral administration, no change of shape in the gastric juice, which means that a drug is not dissolved and a pharmaceutically active ingredient is not dissolved until after a predetermined time following passage through the stomach, irrespective of the length of the residence time in the stomach, but upon lapse of the predetermined time, quickly releases the pharmaceutically active ingredient in the lower part of the gastrointestinal tract to achieve sufficiently effective blood concentration. Particularly, it is characterized in that the time after passage through the stomach till the start of the dissolution can be adjusted as desired by changing the gelling rate and permeability of the material contained in the male piece, which gels in the intestinal juice, and the thickness of the male piece (e.g., mixing ratio of an ethyl acrylate-methyl methacrylate-trimethylammonioethyl methacrylate chloride copolymer and a methacrylic acid-ethyl acrylate copolymer contained in the plug and/or thickness of the plug). Therefore, radical dissolution occurs in a pulse manner after a predetermined time following discharge from the stomach, thereby enabling ensured dissolution of the drug at a predetermined site in the bowels. Consequently, a drug can act effectively at a local site in the lower part of the small bowel, the large bowel and the like, and the drug can be delivered to the lower part of the small bowel or the large bowel without undergoing decomposition of peptides and proteins. In addition, since the present preparation can enclose a maximum amount of an active substance in a capsule having a given size, it is particularly useful as an oral administration dosage form for human and animal.

This application is based on application No. 28365/1998 filed in Japan, the contents of which are incorporated hereinto by reference.

What is claimed is:

1. A controlled release preparation comprising at least one kind of a pharmaceutically active ingredient, a male piece and a female piece, the pieces fitting together to enclose the active substance therein, wherein the male piece is a copolymer that does not swell in water but gels in the intestinal juice.

2. The controlled release preparation of claim 1, wherein the male piece comprises, as the material that gels in the intestinal juice, an ethyl acrylate-methyl methacrylate-trimethylammonioethyl methacrylate chloride copolymer and a methacrylic acid-ethyl acrylate copolymer.

3. The controlled release preparation of claim 2, wherein the ethyl acrylate-methyl methacrylate-trimethylammonioethyl methacrylate chloride copolymer has a copolymerization ratio (ethyl acrylate:methyl methacrylate:trimethylammonioethyl methacrylate chloride (molar ratio)) of 1:2:0.1–0.2.

4. The controlled release preparation of claim 2, wherein the methacrylic acid-ethyl acrylate copolymer has a copolymerization ratio (methacrylic acid:ethyl acrylate (molar ratio)) of 1:1.

5. The controlled release preparation of claim 2, wherein the ethyl acrylate-methyl methacrylate-trimethylammonioethyl methacrylate chloride copolymer has a copolymerization ratio (ethyl acrylate:methyl methacrylate:trimethylammonioethyl methacrylate chloride (molar ratio)) of 1:2:0.1–0.2 and the methacrylic acid-ethyl acrylate copolymer has a copolymerization ratio (methacrylic acid:ethyl acrylate (molar ratio)) of 1:1.

6. The controlled release preparation of claim 2, wherein the methacrylic acid-ethyl acrylate copolymer is contained in a proportion of 0.3–20 parts by weight per part by weight of the ethyl acrylate-methyl methacrylate-trimethylammonioethyl methacrylate chloride copolymer.

7. The controlled release preparation of claim 1, wherein the female piece is made from a water insoluble polymer.

8. The controlled release preparation of claim 1, wherein the preparation has a dosage form of a tablet or a capsule.

* * * * *